(12) United States Patent
Guise et al.

(10) Patent No.: US 6,297,290 B2
(45) Date of Patent: *Oct. 2, 2001

(54) COMPOSITION CONTAINING A NERVE FIBER REACTIVITY MODULATING COMPOUND

(75) Inventors: Anne-Emmanuelle Guise; Josiane Allec, both of Antibes; Karen Ctorza, Cagnes sur Mer, all of (FR)

(73) Assignee: Centre International de Recherches Dermatoloques Galderma (C.I.R.D. Galderma), Valbonne (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,125
(22) PCT Filed: May 6, 1997
(86) PCT No.: PCT/FR97/00810
§ 371 Date: Sep. 4, 1998
§ 102(e) Date: Sep. 4, 1998
(87) PCT Pub. No.: WO97/41893
PCT Pub. Date: Nov. 13, 1997

(30) Foreign Application Priority Data

May 6, 1996 (FR) .................................................. 9605641

(51) Int. Cl.[7] .................................................. A61K 31/16
(52) U.S. Cl. .......................... 514/817; 514/818; 514/626; 514/277; 514/315; 514/532; 514/544
(58) Field of Search ..................................... 514/817, 818, 514/626, 277, 315, 532, 544; 424/443, 445, 449

(56) References Cited

U.S. PATENT DOCUMENTS 5,013,545 * 5/1991 Blackman et al. ..................... 424/81
5,098,717 3/1992 Blackman ............................. 514/648

FOREIGN PATENT DOCUMENTS 63-201118 8/1988 (JP) .
94 01087 1/1994 (WO) .

OTHER PUBLICATIONS

Database WPI, Section Ch. Week 8547, Derwent Publications Ltd., London, GB; Class B05, AN 85–294344, XP0020232344 & RO 86 590 A ( Inst Medicina Farm), Apr. 30, 1985.

* cited by examiner

Primary Examiner—Zohreh Fay
Assistant Examiner—C. Delacroix-Muirheid
(74) Attorney, Agent, or Firm—Burns, Doane, Swecker & Mathis, L.L.P.

(57) ABSTRACT

The present invention relates to a novel aqueous composition based on a compound modulating the reactivity of nerve fibers. It relates more particularly to a pharmaceutical composition for topical use on a human or animal body and intended to anesthetize the skin or the mucous membranes or to treat pruritus.

15 Claims, No Drawings

COMPOSITION CONTAINING A NERVE FIBER REACTIVITY MODULATING COMPOUND

This application is a 371 of PCT/FR97/00810 filed May 6, 1997.

The present invention relates to a novel aqueous composition based on a compound modulating the reactivity of nerve fibers. It relates more particularly to a pharmaceutical composition for topical use on a human or animal body and intended to anesthetize the skin or the mucous membranes or to treat pruritus.

For many years, it has been attempted to make active compounds, such as local anesthetics or antipruritic agents, penetrate into the epidermis or to the dermo-epidermal junction. Thus, on the one hand, methods using the iontophoresis technique which, however, turns out to be relatively complex, and on the other hand special formulations, were proposed.

Among these special formulations, there have been proposed, for example, compositions in the form of cream, based on a eutectic mixture of local anesthetics. However, these compositions, although efficacious, have the disadvantages of being complicated to prepare and of having to use a combination of local anesthetics and thus of having to make a compromise between the toxicity and the efficacy of the local anesthetics available to date. In addition, these compositions demand, to obtain an anesthetics effect which is satisfactory in terms of time and/or in quality, a relatively long occlusion time (at least 1 hour), which can turn out to be not very practical for the user (patient) and/or for the physician who has prescribed this anesthesia.

Thus, the aim of the present invention is to propose a composition for topical use which is easy to apply on a human or animal body and in particular a composition which does not necessarily demand a long occlusion time.

The aim of the present invention is likewise to propose a composition allowing local anesthesia or a pruritus treatment which is efficacious in terms of duration and/or in quality to be obtained by topical application of this composition.

The aim of the present invention is finally to propose a composition having low, or even zero, toxicity.

These aims and others are thus achieved by the present invention which relates to an aqueous composition, characterized in that it comprises at least one compound (1) modulating the reactivity of nerve fibers, at least one compound (2) which is water-miscible, solubilize the compound (1) and is volatile, the weight ratio water/volatile compounds being greater than or equal to 0.8, the composition being devoid of any compound, other than water, which does not solubilize the compound (1) and is capable of retarding the evaporation of the volatile compounds present in the composition and devoid of compound which solubilizes the compound (1) and is non-volatile.

This composition has the advantages of being easy to prepare and of a low production cost while retaining a satisfactory anesthetic efficacy.

Compound (1) modulating the reactivity of nerve fibers is understood according to the invention as meaning any compound modulating, locally, nerve conduction. More particularly, these compounds inhibit nervous conduction. Among these compounds, it is possible to mention the local anesthetics and the antipruritic agents.

Among the antipruritic agents, it is possible especially to mention crotamiton.

Local anesthetics are compounds which produce a reversible loss of sensation by inhibiting nerve conduction or by decreasing the excitability of the nerve at the level of their site of application. They can also be described as local analgesics because they are often used to cause a decrease in pain without loss of nerve control.

It is possible especially to mention local anesthetics of the amide type, such as lidocaine, bupivacaine, etidocaine, prilocaine and cinchocaine, ester local anesthetics of benzoic acid, such as amylocaine and propanocaine, ester local anesthetics of para-aminobenzoic acid, such as tetracaine, benzocaine, butacaine, oxybuprocaine, parethoxycaine and procaine, or alternatively other anesthetics, such as diperodon, ketocaine, pramoxine, dimethisoquine and myrtecaine.

Among the local anesthetics mentioned above, it is preferred to use lidocaine.

Advantageously, the local anesthetics are used in their non-ionized form.

They can be used on their own or as a mixture.

The compound (1) in the composition is advantageously present in a concentration of between 0.5 and 30%, and preferably between 3 and 10%, by weight in relation to the total weight of the composition.

Volatile compound is understood according to the invention as meaning any compound, other than water, which volatilizes at a temperature which is lower than or equal to that of the skin (which is generally at approximately 32° C.).

Preferably, the weight ratio water/volatile compounds is greater than or equal to 1.

Generally speaking, the composition according to the invention comprises at least one compound solubilizing the compound (1) in a sufficient quantity such that the compound (1) present does not recrystallize when the composition is applied to the skin. Preferably, this quantity is sufficient such that the compound (1) present in the composition does not recrystallize on storage.

The person skilled in the art knows how to adjust this quantity of solubilizing compound(s) in the composition, knowing that, of course, it varies according to the nature and the quantity of the compound (1) present.

The composition according to the invention does not comprise a compound which solubilizes the compound (1) and is non-volatile, such as dimethyl sulphoxide (DMSO), dimethylacetamide (DMAC), dimethylformamide (DMF), dimethyllactamide, propylene glycol (PG), polyethylene glycol (PEG), dimethylisosorbide (DMIS) and ethoxydiglycol (Transcutol® sold by Gattefossé). These compounds, if they are present in the composition, cause a decrease in the efficacy of the composition.

The composition according to the invention thus comprises, as compound solubilizing the compound (1), only compounds (2).

Among the compounds (2) which are water-miscible, solubilize the compound (1) and are volatile, it is possible especially to mention the $C_1$–$C_6$ alcohols and acetone, which can be used on their own or as a mixture.

Preferably, $C_1$–$C_4$ alcohols are used.

Among $C_1$–$C_4$ alcohols, it is possible to mention ethanol and isopropanol. Ethanol is particularly preferred.

The compound (2) in the composition is advantageously present in a concentration of between 10 and 50%, preferably 10 to 40%, by weight in relation to the total weight of the composition.

The composition according to the invention is devoid of any compound, other than water, which does not solubilize the compound (1) and is capable of retarding the evaporation of the volatile compounds present in the composition; thus, it is devoid of compounds such as certain polyols which do not solubilize the compound (1), such as glycerol and sorbitol. These compounds are excluded because they can decrease the efficacy of the composition.

The composition according to the invention can additionally comprise at least one thickener of natural or synthetic origin. As thickeners, it is possible to mention carboxyvinyl polymers (carbomer), acrylic copolymers such as copolymers of acrylates/alkylacrylates, poly(meth)acrylates of glycerol such as the product sold under the name Norgel by Guardian, polyacrylamides and especially the mixture of polyacrylamide, C13–C14 isoparaffin and Laureth-7, sold under the name Sepigel 305 by Seppic, polysaccharides such as alkylcelluloses and hydroxyalkylcelluloses, natural rubbers (xanthan), clays and anhydrous colloidal silicas, such as Aerosil® sold by Degussa.

Certain of these thickeners can necessitate the addition of a neutralizing agent to favour the thickening of the gel, such as amines or sodium hydroxide.

Thus, the composition according to the invention can be present in liquid, semi-solid or gel form.

The composition according to the invention can moreover comprise all the ingredients conventionally used in the cosmetic or dermatological field, in customary concentrations. These ingredients are in particular chosen from preservatives, perfumes, surfactants, antioxidants, fillers, filters, humectants and mixtures thereof.

The composition can also be formulated in aerosol composition form likewise comprising a propellant under pressure.

It is possible, among other things, to add active agents intended especially to prevent and/or to treat cutaneous disorders. Among these active agents, it is possible to mention by way of example:

agents modulating cutaneous differentiation and/or proliferation and/or pigmentation, such as vitamin D and its derivatives, retinoic acid and its analogues, estrogens such as estradiol, kojic acid or hydroquinone;

antibacterials such as clindamycin phosphate, erythromycin or antibiotics of the tetracycline class;

antifungals, in particular compounds belonging to the imidazoles class such as econazole, ketoconazole or miconazole or their salts, polyene compounds, such as amphotericin B, compounds of the allylamine family, such as terbinafine, or alternatively octopirox;

steroidal antiinflammatory agents, such as hydrocortisone, anthralins (dioxyanthranol), anthranoids, betamethasone valerate or clobetasol propionate;

anti-free radical agents, such as alpha-tocopherol or its esters, superoxide dismutases, certain metal chelating agents or ascorbic acid and its esters;

antiseborrheic agents such as progesterone;

antiacne agents such as benzoyl peroxide;

antiseptics;

antihistamines such as diphenhydramine;

vanilloid derivatives such as capsaicin, resiniferratoxin and their analogues;

cicatrizants;

virostatics and/or virucides such as pencyclovir, vidarabin, ibacibabin and their α and β interferons;

agents modulating the release of the neuromediators.

Of course, the person skilled in the art will take care to choose the possible compound(s) to be added to the composition according to the invention in such a way that the advantageous properties attached intrinsically to the composition according to the invention are not, or are not substantially, adversely affected by the proposed addition.

The composition according to the invention can thus be used as a medicament, especially intended to anesthetize the skin or the mucous membranes or to treat pruritus. However, it can also be intended to anesthetize animals, such as insects.

Local anesthesia can be carried out before puncture with a needle (venous, arterial or lumbar), before certain interventions in dermatology (curettage of superficial lesions, cryotherapy, laser treatment of flat angiomas), or alternatively before other interventions such as those on the tympanum.

Of course, the use of this composition on the skin or the mucous membranes can also serve to decrease, preventively or preferably curatively, pain connected with pathologies such as ulcers or burns, or to decrease, preventively or curatively, itching (pruritus) connected especially with insect stings.

The method of use of the composition according to the invention corresponds to the customary use techniques of this type of compositions.

Thus, the composition is generally applied to the part (skin or mucous membranes) to be treated, then can be advantageously kept in position by an adhesive patch. The adhesive patch can allow partial or total occlusion of the composition on the part to be treated. It is possible, for example, to use, as adhesive dressing, the product Tegaderm® sold by Laboratoires 3M Santé or, as adhesive patch, the product Finn Chambers® sold by Promédica.

According to this method, the composition of the invention has the advantage of being efficacious at the end of only 30 minutes. The composition can, however, be kept in position for longer without losing its efficacy.

The following examples illustrate the invention. In these examples, the proportions indicated are percentages by weight.

EXAMPLES

Example 1

| Lidocaine base (non-ionized form) | 5 |
|---|---|
| Water | 55 |
| Absolute ethanol | 39 |
| Klucef HF (hydroxypropylcellulose) | 1 |

This composition is prepared by addition and simple mixing of these compounds.

The weight ratio water/volatile compounds is equal to 1.4.

Example 2

| Tetracaine base | 5 |
|---|---|
| Methocel E4M ® (hydroxypropylmethylcellulose) | 1 |
| Water | 52 |
| Absolute ethanol | 42 |

This composition is prepared by addition and simple mixing of these compounds.

The weight ratio water/volatile compounds is equal to 1.2.

Example 3

| Lidocaine base (non-ionized form) | 5 |
|---|---|
| Water | 52 |
| 95/96% Rectapur ethanol | 40 |
| Natrasol 250 HHX Pharm (hydroxyethylcellulose) | 3 |

This composition is prepared by addition and simple mixing of these compounds.

The weight ratio water/volatile compounds is equal to 1.4.

Example 4
Evaluation of the Anesthetic Effect

The anesthetic effect of the composition of Example 3 was evaluated by applying it topically, blind, to individuals and comparing it with that of its vehicle (without lidocaine base).

Each composition was applied on the forearm (three sites on each forearm) of 24 healthy volunteers by using an adhesive plaster: 3M Micropore® with a concentration of the composition of 1.5 g/10 cm² for a determined period.

For each of these applications, an evaluation of the anesthetic effect was carried out by using the prick test with a needle immediately after having removed the adhesive patch which was kept on for 0, 15, 30 or 60 minutes. The greater the number of pricks to obtain a sensation of pain, the greater the anesthetic effect.

The anesthetic effect of the composition of Example 3 applied for 30 minutes is statistically greater than that of its vehicle (composition of Example 3, without lidocaine) applied for 60 minutes. The anesthetic effect of the composition of Example 3 applied for 60 minutes is statistically greater than that of the composition of Example 3 applied for 30 minutes.

The cream EMLA® of Astra® laboratories with Tegaderm® as adhesive plaster, used under the same conditions and in the same concentration (1.5 g/10 cm²), statistically gives results equivalent to the composition of Example 3 with 3M Micropore® as adhesive plaster. A significant anesthetic effect continues, in the two cases, between 15 and 60 minutes after removal of the plaster.

What is claimed is:

1. A method for anesthetizing the skin or the mucous membranes or for treating pruritus in a human or other animal in need of same, said method comprising topically applying to the surface of the skin or mucous membranes of said human or other animal an aqueous composition comprising water, an anesthetically or antipruritically effective amount of at least one compound (1) which modulates the reactivity of nerve fibers, at least one compound (2) which is water-miscible, solubilizes the compound (1), is volatile and is present in sufficient quantity to prevent recrystallization of the compound (1) when the composition is applied to the surface of the skin, and at least one thickener, the weight ratio of water/volatile compounds being greater than or equal to 0.8, the compound (2) being present in a concentration of between 10 and 50% by weight relative to the total weight of the composition, the composition being devoid of any compound, other than water, which does not solubilize the compound (1) and is capable of retarding the evaporation of the volatile compounds present in the composition, and devoid of a compound which solubilizes the compound (1) and is nonvolatile.

2. The method according to claim 1, wherein the compound (1) is a local anesthetic.

3. The method according to claim 2, wherein the local anesthetic is selected from the group consisting of lidocaine, bupivacaine, etidocaine, prilocaine, cinchocaine, amylocaine, propanocaine, tetracaine, benzocaine, butacaine, oxybuprocaine, parethoxycaine, procaine, diperodon, ketocaine, pramoxine, dimethisoquine and myrtecaine.

4. The method according to claim 3, wherein the local anesthetic is lidocaine.

5. The method according to claim 1, wherein the compound (1) is present in a concentration of between 0.5% and 30% by weight in relation to the total weight of the composition.

6. The method according to claim 5, wherein the compound (1) is present in a concentration of between 3% and 10% by weight in relation to the total weight of the composition.

7. The method according to claim 1, wherein the compound (2) is a $C_1$–$C_6$ alcohol or acetone.

8. The method according to claim 7, wherein the compound (2) is a $C_1$–$C_4$ alcohol.

9. The method according to claim 8, wherein the compound (2) is ethanol.

10. The method according to claim 1, wherein the weight ratio of water/volatile compounds is greater than or equal to 1.

11. The method according to claim 10, wherein the compound (2) is present in a concentration of between 10 and 40% by weight in relation to the total weight of the composition.

12. The method according to claim 1, wherein the composition is topically applied to the surface of the skin or mucous membranes using an adhesive patch which provides for partial or total occlusion of the composition on the part of the skin or mucous membrane which is being treated.

13. The method according to claim 12, wherein the patch is kept in contact with the skin or mucous membranes for at least 15 minutes.

14. The method according to claim 1, which is effected to anesthetize the skin or the mucous membranes.

15. The method according to claim 1, which is effected for the treatment of pruritus.

* * * * *